US012788343B2

(12) United States Patent
Guo et al.

(10) Patent No.: US 12,788,343 B2
(45) Date of Patent: Nov. 10, 2026

(54) OPERATING METHOD FOR MEDICAL IMAGING SYSTEM, AND MEDICAL IMAGING SYSTEM

(71) Applicant: GE Precision Healthcare LLC, Waukesha, WI (US)

(72) Inventors: Zhaohua Guo, Beijing (CN); Yan Wang, Beijing (CN); Aizhen Zhou, Beijing (CN); Tingting Yue, Beijing (CN); Ziyi Yuan, Beijing (CN); Yong Xu, Beijing (CN); Raghuvaran Periaswamy, Bengaluru (IN); Rakesh Bhat, Bengaluru (IN); Niketa Agarwal, Bengaluru (IN); Sai Kumar Pennujuru, Bengaluru (IN); Shaguftaparvin Chapalgaonkar, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 169 days.

(21) Appl. No.: 18/767,853

(22) Filed: Jul. 9, 2024

(65) Prior Publication Data

US 2025/0017540 A1 Jan. 16, 2025

(30) Foreign Application Priority Data

Jul. 14, 2023 (CN) ......................... 202310870886.4

(51) Int. Cl.
*A61B 6/46* (2024.01)
*A61B 6/00* (2024.01)
(Continued)

(52) U.S. Cl.
CPC ............ *A61B 6/469* (2013.01); *A61B 6/4417* (2013.01); *A61B 6/4452* (2013.01);
(Continued)

(58) Field of Classification Search
CPC ....... A61B 6/0407; A61B 6/08; A61B 6/4233; A61B 6/4411; A61B 6/4417;
(Continued)

(56) References Cited

U.S. PATENT DOCUMENTS 9,814,435 B2 11/2017 Kim
10,966,675 B2 4/2021 Kim
(Continued)

FOREIGN PATENT DOCUMENTS

EP 3185773 B1 1/2020

OTHER PUBLICATIONS

EP application 24187608.5 filed Jul. 10, 2024—extended Search Report issued Nov. 12, 2024; 10 pages.

*Primary Examiner* — Mark R Gaworecki

(57) ABSTRACT

A medical imaging system includes a camera to obtain a captured image including a subject under examination, a display for displaying a graphical user interface including the captured image, and a first boundary indication and a second boundary indication for superimposing and displaying an exposure region on the captured image, an input device for receiving an input operation for adjusting a position of the first boundary indication and an input operation for adjusting a position of the second boundary indication, and a controller for determining the position of the first boundary indication and the position of the second boundary indication according to the input operations received by the input device, and determining a position of an anatomical site. When the position of the anatomical site changes in the captured image, the position of the first boundary indication and the position of the second boundary indication change.

18 Claims, 7 Drawing Sheets

(51) Int. Cl.
*A61B 6/04* (2006.01)
*A61B 6/08* (2006.01)

(52) U.S. Cl.
CPC ............ *A61B 6/4464* (2013.01); *A61B 6/463* (2013.01); *A61B 6/465* (2013.01); *A61B 6/488* (2013.01); *A61B 6/5241* (2013.01); *A61B 6/542* (2013.01); *A61B 6/544* (2013.01); *A61B 6/0407* (2013.01); *A61B 6/08* (2013.01); *A61B 6/4411* (2013.01)

(58) Field of Classification Search
CPC ..... A61B 6/4452; A61B 6/4464; A61B 6/463; A61B 6/465; A61B 6/467; A61B 6/469; A61B 6/488; A61B 6/5241; A61B 6/542; A61B 6/544
See application file for complete search history.

(56) References Cited

U.S. PATENT DOCUMENTS

| | | | | |
|---|---|---|---|---|
| 2016/0058403 A1* | 3/2016 | Kim | ....................... | A61B 6/467<br>378/98.2 |
| 2021/0186446 A1 | 6/2021 | Kim | | |

* cited by examiner

OPERATING METHOD FOR MEDICAL IMAGING SYSTEM, AND MEDICAL IMAGING SYSTEM

CROSS-REFERENCE TO RELATED APPLICATIONS

This application is based on and claims priority to Chinese Patent Application No. 202310870886.4, filed on Jul. 14, 2023, the entire contents of which is herein incorporated by reference.

TECHNICAL FIELD

Embodiments of the present application relate to the technical field of medical imaging, and relate in particular to an operating method for a medical imaging system, and a medical imaging system.

BACKGROUND

In a medical imaging system, emitted X-rays from an X-ray source are directed at a subject under examination and are received by a detector after penetrating the subject under examination. The detector is divided into an array of discrete elements (such as pixels). The detector elements are read to produce an output signal on the basis of the amount or intensity of radiation impinging on each pixel region. The signal is processed to produce a medical image of the subject under examination, and the medical image can be displayed in a display of the medical imaging system.

SUMMARY

Embodiments of the present application provide an operating method of a medical imaging system, and a medical imaging system.

According to one aspect of the embodiments of the present application, a medical imaging system is provided. The medical imaging system includes an imaging device including an X-ray source and a detector, wherein the X-ray source and the detector are capable of cooperating to acquire a medical image of a subject under examination, a camera operably connected to the imaging device for capturing the subject under examination to obtain a captured image including the subject under examination, a display operably connected to the camera for displaying a graphical user interface including the captured image, and a first boundary indication and a second boundary indication for superimposing and displaying an exposure region on the captured image, an input device operably connected to the display for receiving an input operation for adjusting a position of the first boundary indication and an input operation for adjusting a position of the second boundary indication, and a controller for determining the position of the first boundary indication and the position of the second boundary indication according to the input operations received by the input device, and determining a position of an anatomical site corresponding to the position of the first boundary indication and the position of the second boundary indication in the captured image. When the position of the anatomical site changes in the captured image, the position of the first boundary indication and the position of the second boundary indication change.

According to one aspect of the embodiments of the present application, a medical imaging system is provided. The medical imaging system includes a display unit including a graphical user interface, the graphical user interface includes a region for displaying a captured image, and a first boundary indication and a second boundary indication for superimposing and displaying an exposure region on the captured image. When the position of an anatomical site corresponding to the position of the first boundary indication and the position of the second boundary indication changes in the captured image, the position of the first boundary indication and the position of the second boundary indication change along with the position of the anatomical site.

According to one aspect of the embodiments of the present application, an operating method for a medical imaging system is provided. The method includes capturing a subject under examination to obtain a captured image comprising the subject under examination. The method also includes displaying a graphical user interface including the captured image, and a first boundary indication and a second boundary indication for superimposing and displaying an exposure region on the captured image. The method also includes receiving an input operation for adjusting a position of the first boundary indication and an input operation for adjusting a position of the second boundary indication. The method also includes determining the position of the first boundary indication and the position of the second boundary indication according to the received input operations, and determining the position of an anatomical site corresponding to the position of the first boundary indication and the position of the second boundary indication in the captured image. When the position of the anatomical site changes in the captured image, the position of the first boundary indication and the position of the second boundary indication change.

With reference to the following description and drawings, specific embodiments of the examples of the present application are disclosed in detail, and the means by which the principles of the examples of the present application can be employed are illustrated. It should be understood that the embodiments of the present application are therefore not limited in scope. Within the scope of the spirit and clauses of the appended claims, the embodiments of the present application comprise many changes, modifications, and equivalents.

BRIEF DESCRIPTION OF THE DRAWINGS

The included drawings are used to provide further understanding of the examples of the present application, which constitute a part of the description and are used to illustrate the embodiments of the present application and explain the principles of the present application together with textual description. Evidently, the drawings in the following description are merely some examples of the present application, and a person of ordinary skill in the art may obtain other embodiments according to the drawings without involving inventive skill. In the drawings.

DETAILED DESCRIPTION

The foregoing and other features of the examples of the present application will become apparent from the following description and with reference to the drawings. In the description and drawings, specific embodiments of the present application are disclosed in detail, and part of the embodiments in which the principles of the examples of the present application may be employed are indicated. It should be understood that the present application is not limited to the described embodiments. On the contrary, the examples of the present application include all modifications, variations, and equivalents which fall within the scope of the appended claims.

In the examples of the present application, the terms "first" and "second" and so on are used to distinguish different elements from one another by their title, but do not represent the spatial arrangement, temporal order, or the like of the elements, and the elements should not be limited by said terms. The term "and/or" includes any one of and all combinations of one or more associated listed terms. The terms "comprise", "include", "have", etc., refer to the presence of stated features, elements, components, or assemblies, but do not exclude the presence or addition of one or more other features, elements, components, or assemblies. The terms "connect", "connected", "couple", as well as other similar terms to which the embodiments of the present application relate are not limited to physical or mechanical connections, but may include electrical connections, whether directly connected or indirectly connected.

In the examples of the present application, the singular forms "a" and "the" or the like include plural forms, and should be broadly construed as "a type of" or "a kind of" rather than being limited to the meaning of "one". Furthermore, the term "the" should be construed as including both the singular and plural forms, unless otherwise specified in the context. In addition, the term "according to" should be construed as "at least in part according to . . . ", and the term "based on" should be construed as "at least in part based on . . . ", unless otherwise clearly specified in the context.

The features described and/or illustrated for one embodiment may be used in one or more other embodiments in an identical or similar manner, combined with features in other embodiments, or replace features in other embodiments. The term "include/comprise" when used herein refers to the presence of features, integrated components, steps, or assemblies, but does not exclude the presence or addition of one or more other features, integrated components, steps, or assemblies.

Figure 1:
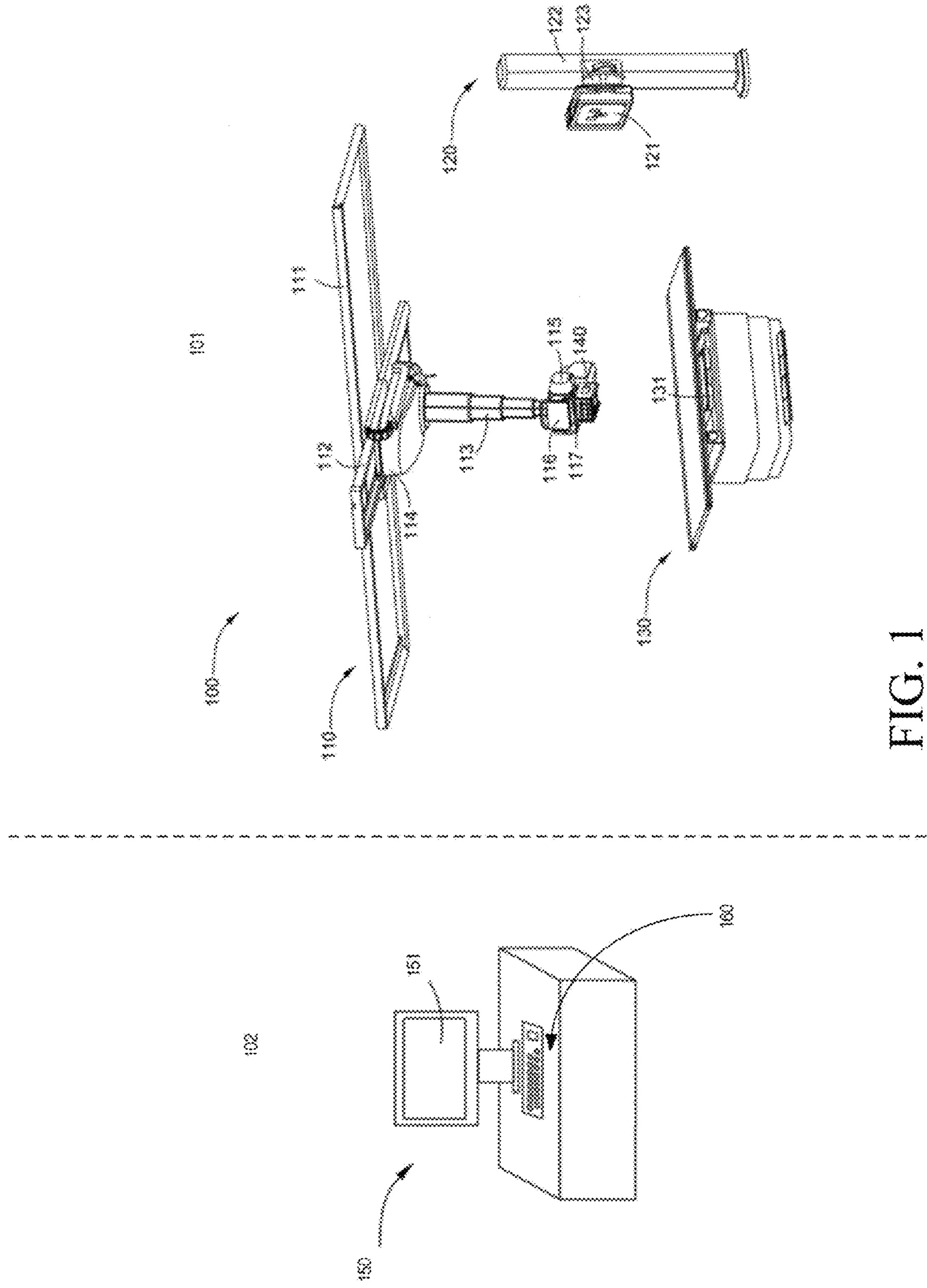
FIG. 1 is a schematic diagram of a medical imaging system of an embodiment of the present application.

FIG. 1 is a medical imaging system 100 of an embodiment of the present application. As shown in FIG. 1, the medical imaging system 100 includes a suspension apparatus 110, a wall stand apparatus 120 and an examination bed apparatus 130 provided in a scanning room 101, and a controller 150 provided in a control room 102. The suspension apparatus 110 includes a longitudinal guide rail 111, a transverse guide rail 112, a telescopic cylinder 113, a sliding member 114, and a tube assembly 115.

Although some embodiments of the present application are described on the basis of a suspended X-ray imaging system, the embodiments of the present application are not limited thereto.

For ease of description, in the present application, an x-axis, y-axis, and z-axis are defined as the x-axis and the y-axis being located in a horizontal plane and being perpendicular to one another, and the z-axis being perpendicular to the horizontal plane. Specifically, the direction in which the longitudinal guide rail 111 is located is defined as the x-axis, the direction in which the transverse guide rail 112 is located is defined as the y-axis direction, and the direction of extension of the telescopic cylinder 113 is defined as the z-axis direction, and the z-axis direction is the vertical direction.

The longitudinal guide rail 111 and the transverse guide rail 112 are perpendicularly arranged, wherein the longitudinal guide rail 111 is mounted on a ceiling, and the transverse guide rail 112 is mounted on the longitudinal guide rail 111. The telescopic cylinder 113 is used to carry the tube assembly 115.

The sliding member 114 is disposed between the transverse guide rail 112 and the telescopic cylinder 113. The sliding member 114 may include components such as a rotary shaft, a motor, and a reel. The motor can drive the reel to rotate around the rotary shaft, which in turn drives the telescopic cylinder 113 to move along the z axis and/or slide relative to the transverse guide rail. The sliding member 114 can slide relative to the transverse guide rail 112, that is, the sliding member 114 can drive the telescopic cylinder 113 and/or the tube assembly 115 to move in the y-axis direction. Furthermore, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of columns having different inner diameters, and the plurality of columns may be sleeved sequentially from bottom to top in columns located thereon to thereby achieve telescoping. The telescopic cylinder 113 can be telescopic (or movable) in the vertical direction, that is, the telescopic cylinder 113 can drive the tube assembly to move along the z-axis direction. The lower end of the telescopic cylinder 113 is further provided with a rotating part, and the rotating part may drive the tube assembly 115 to rotate.

The tube assembly 115 includes an X-ray tube, and the X-ray tube may produce X-rays and project the X-rays to a patient's intended region of interest (ROI). Specifically, the X-ray tube may be positioned adjacent to a beam limiter, and the beam limiter is used to align the X-rays with the patient's intended region of interest. At least part of the X-rays may be attenuated by means of the patient and may be incident on a detector 121/131.

The suspension apparatus 110 further includes a beam limiter 117, which is usually mounted below the X-ray tube, and the X-rays emitted by the X-ray tube are irradiated onto the body of a subject under examination by means of an opening of the beam limiter 117. The size of the opening of the beam limiter 117 determines an irradiation range of the X-rays, namely, the size of a region of an exposure field of view (FOV). The positions of the X-ray tube and beam limiter 117 in the transverse direction determine the position of the exposure FOV on the body of the subject under examination. It is well known that X-rays are harmful to the human body, so it is necessary to control the X-rays so that the same only irradiate a site of the subject under examination that needs to be examined, namely, a region of interest (ROI).

The suspension apparatus 110 further includes a tube controller (console) 116. The tube controller 116 is mounted on the tube assembly. The tube controller 116 includes user interfaces such as a display screen and a control button for performing preparation work before image capture, such as patient selection, protocol selection, positioning, etc.

The movement of the suspension apparatus 110 includes the movement of the tube assembly along the x-axis, y-axis, and z-axis, as well as the rotation of the tube assembly in a horizontal plane (the axis of rotation is parallel to or coincides with the z-axis) and in a vertical plane (the axis of rotation is parallel to the y-axis). In the described movement, a motor is usually used to drive a rotary shaft which in turn drives a corresponding component to rotate, so as to achieve a corresponding movement or rotation, and a corresponding control component is generally mounted in the sliding member 114. An X-ray imaging unit further includes a motion control unit (not shown in the figure), and the motion control unit can control the described movement of the suspension apparatus 110. Furthermore, the motion control unit can receive a control signal to control a corresponding component to move correspondingly.

The wall stand apparatus 120 includes a first detector assembly 121, a wall stand 122, and a connecting portion 123. The connecting portion 123 includes a support arm that is vertically connected in the height direction of the wall stand 122 and a rotating bracket that is mounted on the support arm, and the first detector assembly 121 is mounted on the rotating bracket. The wall stand apparatus 120 further includes a detector driving apparatus that is provided between the rotating bracket and the first detector assembly 121. Under the drive of the detector driving apparatus, the first detector assembly 121 moves along a direction that is parallel to the height direction of the wall stand 122 in a plane that is supported by the rotating bracket, and the first detector assembly 121 may be further rotated relative to the support arm to form an angle with the wall stand. The first detector assembly 121 has a plate-like structure the orientation of which can be changed, so that the incident surface of the X-rays becomes vertical or horizontal depending on the incident direction of the X-rays.

A second detector assembly 131 is included on the examination bed apparatus 130, and the selection or use of the first detector assembly 121 and the second detector assembly 131 may be determined on the basis of an image capture site of a patient and/or an image capture protocol, or may be determined on the basis of the position of the subject under examination that is obtained by the capturing of a camera, so as to perform image capture and examination at a supine, prone, or standing position. FIG. 1 merely shows a schematic diagram of a wall stand and an examination bed. It should be understood by those skilled in the art that a wall stand and/or examination bed in any form or arrangement may be selected or just the wall stand can be mounted, and the wall stand and/or examination bed do/does not limit the entire solution of the present application.

In some embodiments, the medical imaging system includes an camera 140 (such as a camera). The subject under examination may be captured by the camera to obtain a captured image that includes the subject under examination, for example a static optical image or a series of optical image frames in a dynamic real-time video stream, to carry out auxiliary positioning, exposure configurations, and the like. The camera may be mounted on the suspension apparatus, for example mounted on a side edge of the beam limiter 117, and the like, and the embodiments of the present application are not limited thereto. The camera 140 includes one or more cameras, such as a digital camera or an analog camera, or a depth camera, an infrared camera or an ultraviolet camera, or a 3D camera or a 3D scanner, or a red, green and blue (RGB) sensor, an RGB depth (RGB-D) sensor or other devices that can capture color image data of a target object.

In some embodiments, the controller 150 may include a source controller and a detector controller. The source controller is used to command the X-ray source to emit X-rays for image exposure. The detector controller is used to select a suitable detector from among a plurality of detectors and to coordinate the control of various detector functions, such as automatically selecting a corresponding detector according to the position or pose of the subject under examination. Alternatively, the detector controller may perform various signal processing and filtering functions, specifically, for initial adjustment of a dynamic range, interleaving of digital image data, and the like. In some embodiments, the controller may provide power and timing signals for controlling the operation of the X-ray source and the detector.

In some embodiments, the controller may also be configured to use a digitized signal to reconstruct one or more required images and/or determine useful diagnostic information corresponding to a patient, wherein the controller may include one or more dedicated processors, graphics processing units (GPUs), digital signal processors, microcomputers, microcontrollers, application-specific integrated circuits (ASICs), field-programmable gate arrays (FPGAs), or other suitable processing apparatuses.

Certainly, the medical imaging system may also include other numbers, configurations, or forms of controllers, for example, the controller may be local (e.g., co-located with one or more medical imaging systems 100, such as within the same facility and/or the same local network). In other implementations, the controller may be remote and thus only accessible by means of a remote connection (for example, by means of the Internet or other available remote access technologies). In a specific implementation, the controller may also be configured in a cloud-like means, and may be accessed and/or used in a means that is substantially similar to the means by which other cloud-based systems are accessed and used.

The system 100 also includes a storage apparatus (not shown in the figure). A processor may store the digitized signal in a memory. For example, the memory may include a hard disk drive, a floppy disk drive, a CD-read/write drive, a digital versatile disc (DVD) drive, a flash drive, and/or a solid-state memory. The memory may also be integrated together with the processor to effectively use the footprint and/or meet expected imaging requirements.

The system 100 further includes an input device 160. The input device 160 may include a certain form of operator interface, such as a keyboard, a mouse, a voice-activated controller, a touch screen (which may also be used a display described later), a tracking ball or any other suitable input device. An operator may input an operating signal/control signal to the controller by means of the input device.

The system 100 further includes a display 151 (such as a touch screen or a display screen). The display 151 may be used to display an operation interface such as a list of subjects under examination, the positioning or exposure configurations of subjects under examination, and images of subjects under examination.

Generally, the size of an obtained medical image is generally equal to the size of the X-ray detector (the exposure field of view). If the region of interest is within the size of the X-ray detector (the exposure field of view), then the entire region of interest can be completely presented in one image. If the region of interest exceeds the size of the X-ray detector (the exposure field of view), then the entire region of interest cannot be completely presented in one image, and it is necessary to divide the region of interest into a plurality of regions, respectively perform exposure imaging on each region, and stitch multiple acquired X-ray images together to acquire a complete medical image. Hereinafter, images obtained by performing X-ray imaging in each region are referred to as sub-medical images, and the complete medical image is also referred to as a combined image or a stitched image.

Currently, it is possible to display, on the display, a captured image obtained by using the camera to capture a subject under examination. The captured image is distinguished from the medical image acquired by performing X-ray imaging, and is used for auxiliary positioning or exposure configurations. For example, the auxiliary positioning or exposure configurations include acquiring information of the subject under examination, acquiring a capture protocol, determining information such as a capture dose and posture, performing positioning on the basis of the capture protocol, setting the size and position of an exposure region, etc. To this end, the embodiments of the present application propose a method, a graphical user interface, and a medical imaging system that can quickly and conveniently set the position of the exposure region.

The embodiments of the present application are specifically described below.

Embodiments of the present application provide a medical imaging system. The system includes: an imaging device, an camera, a display, an input device, and a controller, the imaging device including an X-ray source and a detector, the X-ray source and the detector being capable of cooperating to acquire a medical image of a subject under examination, the camera capturing the subject under examination to acquire a captured image including the subject under examination, and the display displaying a graphical user interface including the captured image. For implementations regarding the imaging device, the camera, the display, the input device and the controller, reference may be made to the foregoing embodiment corresponding to FIG. 1, and repeated descriptions will not be given herein, and the differences will be specifically described below.

Figure 2:
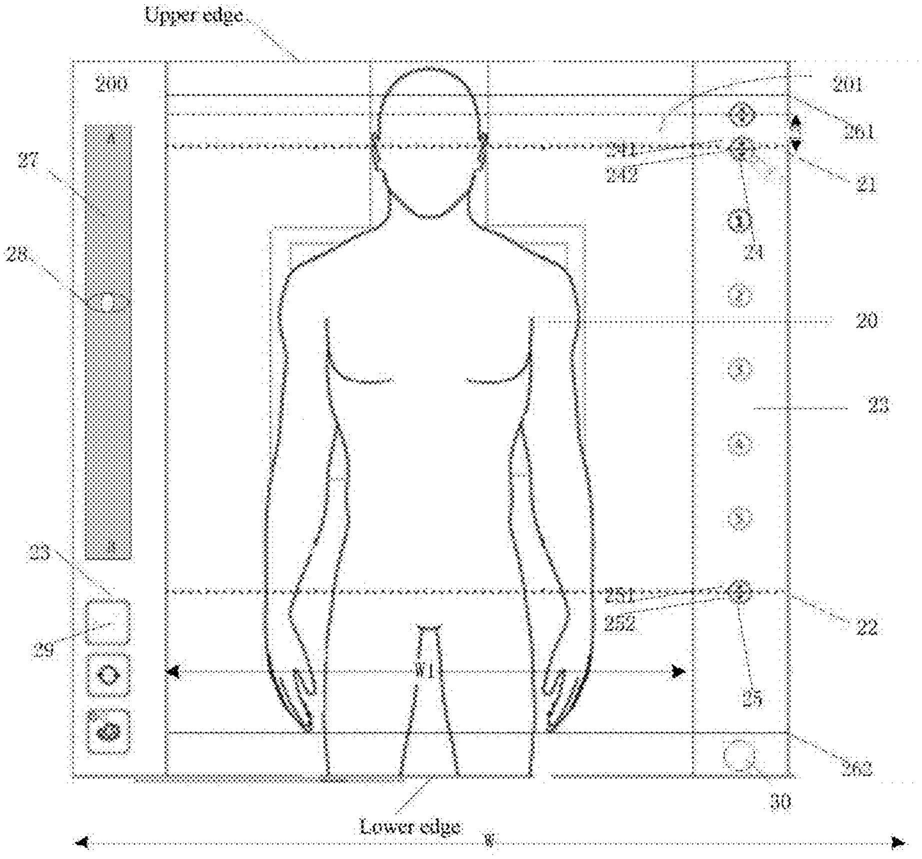
FIG. 2 is a schematic diagram of a graphical user interface of an embodiment of the present application.

FIG. 2 is a schematic diagram of a graphical user interface displayed by a display according to an embodiment of the present application. As shown in FIG. 2, the graphical user interface 200 includes a first region 201 displaying a captured image 20, and a first boundary indication 21 and a second boundary indication 22 for superimposing and displaying an exposure region on the captured image 20. The captured image may be a still image, or an image frame in a video stream acquired in real time. The outer side of the captured image in the first region 201 may further include an operating region 23, and some graphic objects for interaction may be included on the operating region, which will be specifically described later. The first boundary indication 21 and the second boundary indication 22 indicate the positions of two boundaries of the exposure region, respectively. For example, the first boundary indication 21 is closer to the position of the head of the subject under examination than the second boundary indication 22 is. In other words, the second boundary indication 22 is closer to the position of the foot of the subject under examination than the first boundary indication is. That is, the first boundary indication 21 is used to indicate the upper boundary of the exposure region, and the second boundary indication 22 is used to indicate the lower boundary of the exposure region. The first boundary indication 21 and the second boundary indication 22 may be displayed as line segments parallel to the width direction W of the captured image (the width direction of the subject under examination). The line segments may be solid lines or dashed lines. The length of the line segments may be equal to the width W1 of the captured image, or longer than the width W1 of the captured image (for example, a line segment of part of the boundary indication is also displayed on the operating region 23), or shorter than the width W1 of the captured image, and the embodiments of the present application are not limited thereto.

The above is merely illustrative. For example, the first boundary indication 21 may be closer to the position of the foot of the subject under examination, and the second boundary indication 22 may be closer to the position of the head of the subject under examination, etc. In addition, in FIG. 2, the captured image is displayed with the head of the subject under examination on the upper side, but the captured image 20 in FIG. 2 may also be displayed in a direction rotated (clockwise or counterclockwise) by 90°. In addition, the first boundary indication 21 and the second boundary indication 22 may also be displayed in a direction rotated (clockwise or counterclockwise) by 90° to define the left boundary and right boundary of the exposure region, etc. The embodiments of the present application are not limited thereto, and no more examples will be given here. The relative position of the first boundary indication 21 and the second boundary indication 22 in FIG. 2 is used as an example below for illustration.

In some embodiments, after the camera obtains the captured image, the display displays the captured image 20, and superimposes and displays the first boundary indication 21 and the second boundary indication 22 on the captured image. For example, during initial display, the controller may determine initial positions of the first boundary indication 21 and the second boundary indication 22 according to the center position on the captured image or a site to be imaged. For example, the controller recognizes the center position on the captured image by using an image recognition algorithm, moves a line segment passing through the center position (parallel to the width direction W of the captured image) upward by a distance L1 to serve as the initial display position of the first boundary indication 21, and moves the line segment passing through the center position (parallel to the width direction W of the captured image) downward by a distance L2 to serve as the initial display position of the second boundary indication 22. The L1 and L2 may be predefined, or may be determined according to the site to be imaged. Alternatively, the controller may determine the initial positions of the first boundary indication 21 and the second boundary indication 22 according to the site to be imaged. For example, when the site to be imaged is the spine, the captured image generally includes the upper half of the body or the whole body of the subject under examination, and the controller uses an image recognition algorithm or artificial intelligence algorithm (e.g., uses a deep learning network) (the captured object is used as the object to undergo recognition) to recognize the position of the person's car, and uses a line segment (parallel to the width direction W of the captured image) passing through the position of the person's car as the initial display position of the first boundary indication 21, and recognizes the position of the person's coccyx, and uses a line segment (parallel to the width direction W of the captured image) passing through the position of the coccyx as the initial display position of the second boundary indication 22. When the site to be imaged is a leg bone, the captured image generally includes the lower half of the body or whole body of the subject under examination, and the controller uses an image recognition algorithm or artificial intelligence algorithm (e.g., uses a deep learning network) (the captured object is used as the object to undergo recognition) to recognize the position of the person's pelvic bone, and uses a line segment (parallel to the width direction W of the captured image) passing through the position of the pelvic bone as the initial display position of the first boundary indication 21, and recognizes the position of the person's ankle bone, and uses a line segment (parallel to the width direction W of the captured image) passing through the position of the ankle bone as the initial display position of the second boundary indication 22. The embodiments of the present application are not limited thereto. For specific implementations regarding the image recognition algorithm or artificial intelligence algorithm, reference may be made to the related art, and the embodiments of the present application are not limited thereto.

The above is an example in which the controller uses an algorithm to automatically generate the initial positions of the first boundary indication 21 and the second boundary indication 22, but the present application is not limited thereto. For example, it is also possible that the initial positions of the first boundary indication 21 and the second boundary indication 22 are initialized according to an initialization input operation received by the input device. That is, after the captured image is displayed, the graphical user interface instructs the operator to perform a position initialization input operation with respect to a boundary indication. The initialization input operation includes a mouse click, a touch screen click, etc., the position of the click may be on the captured image 20 or on the operating region 23, and a line segment (parallel to the width direction W of the captured image) passing through the click position is used as the initial position of the boundary indication. In this way, the operator may customize the initial position of the first boundary indication 21 or the second boundary indication 22. In this example, the operator may initialize the initial positions of the first boundary indication 21 and the second boundary indication 22, or the operator may initialize only the initial position of one of the first boundary indication 21 and the second boundary indication 22, and the position of the other boundary indication may be automatically generated according to the customized position of the boundary indication. For example, the distance between the first boundary indication 21 and the second boundary indication 22 is predefined as LD, and then the controller may obtain a position by moving upward or downward by the distance LD according to the customized position of the boundary indication and use the same as the position of the other boundary indication.

In some embodiments, the controller may use the foregoing initial positions of the first boundary indication and the second boundary indication as final positions to determine the size of the exposure region, that is, it is not necessary to adjust the positions of the first boundary indication and the second boundary indication (for example, the input device receives input operations for determining (locking) the positions of the first boundary indication and the second boundary indication, and the controller locks the position of the first boundary indication and the position of the second boundary indication, indicating that the position of the first boundary indication and the position of the second boundary indication cannot be adjusted again. The input operations will be described later). In some embodiments, when the subject under examination moves or the viewable range of the camera changes, or when the operator determines that the currently displayed exposure region is inaccurate or imprecise, the operator may adjust the positions of the first boundary indication 21 and the second boundary indication 22 superimposed and displayed on the captured image, and the display may update and display, according to the adjustment, the adjusted positions of the first boundary indication 21 and the second boundary indication 22 on the captured image in real time. The input device may receive at least one of an input operation for adjusting the position of the first boundary indication and an input operation for adjusting the position of the second boundary indication. The controller may use the adjusted position of the first boundary indication and the adjusted position of the second boundary indication as final positions to determine the size of the exposure region (for example, the input device receives input operations for determining (locking) the positions of the first boundary indication and the second boundary indication, and the controller locks the position of the first boundary indication and the position of the second boundary indication, indicating that the position of the first boundary indication and the position of the second boundary indication cannot be adjusted again).

In some embodiments, after the controller determines (locks) the position of the first boundary indication and the position of the second boundary indication, there may still be a certain time interval before the exposure, during which the subject under examination may move, resulting in a change in the exposure region determined by the first boundary indication and the second boundary indication. In this way, in the embodiments of the present application, the controller determines the position of an anatomical site corresponding to the position of the first boundary indication and the position of the second boundary indication in the captured image, and when the position of the anatomical site changes in the captured image, the position of the first boundary indication and the position of the second boundary indication change along with the position of the anatomical site, thereby avoiding errors caused by movement of the subject under examination.

In some embodiments, the controller may determine the position of the anatomical site corresponding to the position of the first boundary indication and the position of the second boundary indication, for example, determines and records the position of an anatomical site (car bone) corresponding to the position of the first boundary indication, and determines the position of an anatomical site (coccyx) corresponding to the position of the second boundary indication. The above positions may be coordinate positions (such as pixel coordinate positions) in the captured image, and the position of the first boundary indication and the position of the second boundary indication changing along with the position of the anatomical site includes: the position of the first boundary indication and the position of the second boundary indication being fixed relative to the position of the anatomical site.

Figure 11:
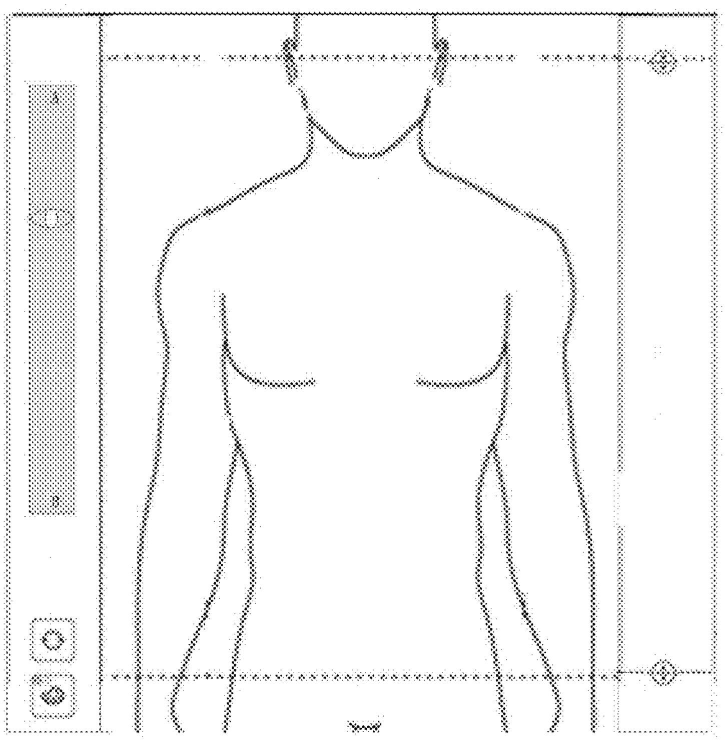
FIG. 11 is a schematic diagram of a graphical user interface according to an embodiment of the present application.

FIG. 11 is a schematic diagram of a graphical user interface according to an embodiment of the present application after the subject under examination moves. As shown in FIG. 11, the subject under examination may move forward (in a direction toward the camera), the captured image displayed by the display will be updated, and the positions of the first boundary indication and the second boundary indication superimposed and displayed on the captured image will also be updated. The subject under examination is enlarged in the captured image, and the position of the car bone moves upward and the position of the coccyx moves downward in the captured image. Thus, the position of the first boundary indication also moves upward along with the position of the car bone, and is always located at the position of the car bone, that is, the position relative to the car bone is fixed; and the position of the second boundary indication also moves downward along with the position of the coccyx, and is always located at the position of the coccyx, that is, the position relative to the coccyx is fixed.

Figure 3:
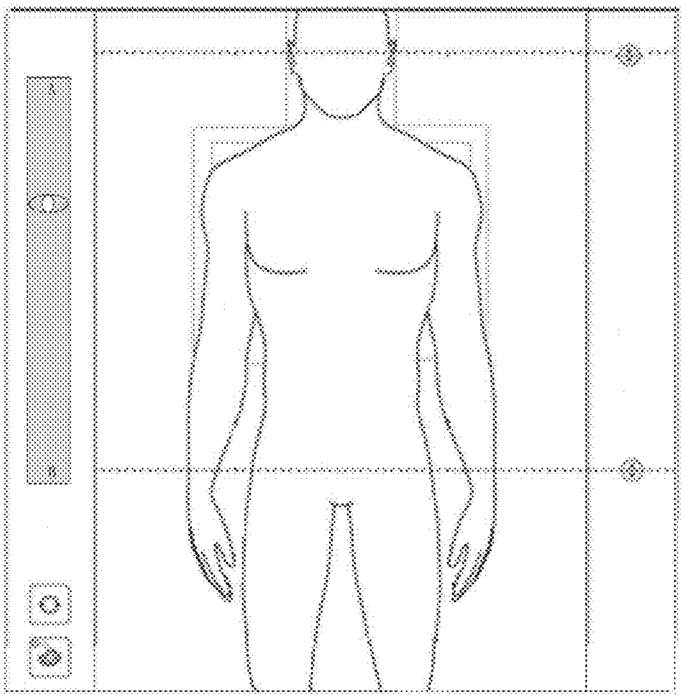
FIG. 3 is a schematic diagram of a graphical user interface of an embodiment of the present application.

In the above example, the movement of the subject under examination results in a change in the position of the subject under examination (the anatomical site) in the captured image, but the embodiments of the present application are not limited thereto. For example, after the viewable range of the camera is adjusted, the position of the subject under examination (the anatomical site) in the captured image may also occur, and when the input device receives an input operation for adjusting the viewable range of the camera, similarly, the position of the first boundary indication and the position of the second boundary indication change along with the position of the anatomical site. The position of the first boundary indication and the position of the second boundary indication are fixed relative to the position of the anatomical site in the captured image. That is, when the viewable range of the camera is adjusted, the captured image displayed by the display will be updated, and the positions of the first boundary indication and the second boundary indication superimposed and displayed on the captured image will also be updated. That is, due to the adjustment of the viewable range of the camera, the position of the anatomical sites (for example, the car bone and the coccyx) in the captured image may change, and the position of the first boundary indication and the position of the second boundary indication in the captured image change in terms of relative position, but are fixed relative to the anatomical site of the subject under examination. FIG. 3 is a schematic diagram of an operation interface after the adjustment of the viewable range of the camera according to an embodiment of the present application. As shown in FIG. 3, in comparison to FIG. 2, after the adjustment of the viewable range of the camera, respective anatomical sites of the subject under examination in the captured image move upward as a whole. Thus, the first boundary indication moves upward along with the position of the car bone and is always located at the position of the car bone of the subject under examination in the captured image, and the first boundary indication is fixed relative to the position of the car bone, and the second boundary indication moves upward along with the coccyx and is always located at the position of the coccyx in the captured image, and the second boundary indication is fixed relative to the position of the coccyx.

Implementations regarding the adjustment of the viewable range of the camera will be described later.

How to adjust the position of the first boundary indication and the position of the second boundary indication will be described below.

In some embodiments, when the input device receives an input operation for adjusting the position of the first boundary indication, the controller controls the position of the second boundary indication to change along with the change of the position of the first boundary indication so that the distance between the first boundary indication and the second boundary indication remains unchanged. In this way, the position of the exposure region can be quickly and conveniently adjusted. The detailed description is provided below.

In some embodiments, the input operation (a first input operation) for adjusting the first boundary indication includes: by means of the input device, triggering the first boundary indication, or triggering a first marker associated with the first boundary indication. The first marker includes a virtual key or other graphical objects, and the first marker may be located on the first boundary indication or on the operating region 23 corresponding to the first boundary indication. The first input operation for triggering includes clicking a corresponding indication or marker by moving a cursor, or touching or operating (e.g., dragging, etc.) the indication or the marker. For example, the first boundary indication is clicked and is then dragged to an adjusted position, or the first boundary indication is clicked and the adjusted position is then clicked, so that the first boundary indication superimposed and displayed on the captured image is changed to the adjusted position along with the input operation. Alternatively, as shown in FIG. 2, the graphical user interface includes a first marker 24 at a position corresponding to the position of the first boundary indication on the operating region 23, and the first marker 24 includes a move-up marker 241 and a move-down marker 242 (after the captured image is rotated by 90°, up and down can be replaced with left and right or right and left, respectively). By clicking on the move-up marker 241, the first boundary indication moves up by a predetermined distance L3, and by clicking on the move-down marker 242, the second boundary indication moves down by the predetermined distance L3. The predetermined distance L3 may be determined as required. For example, during coarse adjustment, the L3 may be set to a first value, and during fine adjustment, the L3 may be set to a second value, the first value being greater than or equal to the second value. The above is only an example for illustration. In addition, the above clicking includes a touch screen click or a mouse click (long press or short press), etc., and the embodiments of the present application are not limited thereto. In this way, the position of the first boundary indication can be quickly adjusted by triggering the first marker on the operating region.

In some embodiments, when the position of the first boundary indication is changed, the controller controls the position of the second boundary indication to change along with the change of the position of the first boundary indication so that the distance between the first boundary indication and the second boundary indication remains unchanged. That is, the position of the second boundary indication moves along with the position of the first boundary indication. During the time in which the indications are superimposed and displayed on the captured image, when the first boundary indication moves up, the second boundary indication also moves up, and when the first boundary indication moves down, the second boundary indication also moves down, and the distance LD between the first boundary indication and the second boundary indication remains unchanged. That is, during the time in which the indications are superimposed and displayed on the captured image, when the first boundary indication moves up by a distance L4, the second boundary indication also moves up by the same distance L4, and when the first boundary indication moves down by the distance L4, the second boundary indication also moves down by the same distance L4. The distance LD may be predefined, and is related to the age, body shape, site to be imaged, etc. of the subject under examination. The embodiments of the present application are not limited thereto. The position of the second boundary indication is controlled to change along with the change of the position of the first boundary indication so that the distance between the first boundary indication and the second boundary indication remains unchanged, thereby simplifying adjustment steps, and quickly and conveniently adjusting the position of the exposure region.

In some embodiments, the input operation (a second input operation) for adjusting the second boundary indication includes: by means of the input device, triggering the second boundary indication, or triggering a second marker associated with the second boundary indication. The second marker includes a virtual key or other graphical objects, and the second marker may be located on the second boundary indication or on the operating region 23 corresponding to the second boundary indication. The second input operation for triggering includes clicking a corresponding indication or marker by moving a cursor, or touching or operating (e.g., dragging, etc.) the indication or the marker. For example, the second boundary indication is clicked and is then dragged to an adjusted position, or the second boundary indication is clicked and the adjusted position is then clicked, so that the second boundary indication superimposed and displayed on the captured image is changed to the adjusted position along with the input operation. Alternatively, as shown in FIG. 2, the graphical user interface includes a second marker 25 at a position corresponding to the position of the second boundary indication on the operating region 23. The implementation of the second marker 25 is similar to that of the first marker 24, and will not be repeated here. By clicking on a move-up marker 251, the second boundary indication moves up by a predetermined distance L5, and by clicking on a move-down marker 252, the second boundary indication moves down by the predetermined distance L5. The predetermined distance L5 may be determined as required, for example, equal to the L3. In addition, the above clicking includes a touch screen click or a mouse click (long press or short press), etc., and the embodiments of the present application are not limited thereto. In this way, the position of the second boundary indication can be quickly adjusted by triggering the second marker on the operating region. In addition, when the position of the second boundary indication is adjusted, the position of the first boundary indication remains unchanged, thereby making the adjustment of the position of the boundary indication more flexible and reducing the time for repeated adjustments.

In some embodiments, when the first input operation and the second input operation adjust the positions of the boundary indications, it is necessary to make the adjustment within the range of the captured image. When the position of the second boundary indication is adjusted to exceed a lower edge of the captured image, the controller restricts downward adjustment of the position of the second boundary indication, and when the position of the first boundary indication is adjusted to exceed an upper edge of the captured image, the controller restricts upward adjustment of the position of the first boundary indication. For example, when the position of the first boundary indication is adjusted to be higher than the upper edge of the captured image, if the move-up marker continues to be clicked or the first boundary indication is dragged upward, then the position of the first boundary indication remains unchanged at the upper edge. When the position of the second boundary indication is adjusted to be lower than the lower edge of the captured image, if the move-down marker continues to be clicked or the second boundary indication is dragged downward, then the position of the second boundary indication remains unchanged at the lower edge.

In addition, when the position of the second boundary indication changes along with the change of the position of the first boundary indication so as to exceed the lower edge of the captured image, the controller controls the position of the second boundary indication to remain unchanged at the lower edge. That is, assuming that the distance between the second boundary indication and the lower edge of the captured image is L6, when the position of the first boundary indication moves downward by a distance greater than L6, the second boundary indication moves downward by the distance L6, that is, moves to a position coincident with the lower edge. If the position of the first boundary indication continues to be adjusted downward, then the second boundary indication remains unchanged at the position coincident with the lower edge. At this time, if the position of the first boundary indication is adjusted upward, the position of the second boundary indication moves upward by the same distance along with the position of the first boundary indication.

In some embodiments, in addition to using the edges of the captured image to restrict the positions of the boundary indications, boundaries beyond which the detector cannot move may also be used to restrict the positions of the boundary indications. This is because the detector does not necessarily cover the entire region of the captured image, and medical images cannot be obtained at positions not coverable by the detector. Therefore, the exposure region needs to be within the boundary range within which the detector can move, or in other words, the boundary range within which the detector can move needs to be able to cover the exposure region. Thus, when the position of the second boundary indication is adjusted to exceed a lower boundary of motion of the detector, the controller restricts downward adjustment of the position of the second boundary indication, and when the position of the first boundary indication is adjusted to exceed an upper boundary of motion of the detector, the controller restricts upward adjustment of the position of the first boundary indication.

For example, when the position of the first boundary indication is adjusted to be higher than the upper boundary of motion of the detector, if the move-up marker continues to be clicked or the first boundary indication is dragged upward, then the position of the first boundary indication remains unchanged at the upper boundary. When the position of the second boundary indication is adjusted to be lower than the lower boundary of motion of the detector, if the move-down marker continues to be clicked or the second boundary indication is dragged downward, then the position of the second boundary indication remains unchanged at the lower boundary.

It should be noted that the detector may be the foregoing first detector assembly, and boundaries beyond which the first detector assembly cannot move include an upper boundary and a lower boundary. However, the embodiments of the present application are not limited thereto. The detector may also be the foregoing second detector assembly, and boundaries beyond which the second detector assembly cannot move include a left boundary and a right boundary. The implementation thereof is similar to that of the upper boundary and the lower boundary, and will not be repeated here.

In some embodiments, in order to reduce the time of unnecessary repeated adjustments, the display may further superimpose and display, on the captured image, at least one of the upper boundary of motion and the lower boundary of motion of the detector. In this way, when adjusting the position of the first boundary indication or the second boundary indication, the operator can refer to the position of the displayed upper or lower boundary to prevent the position of the first boundary indication or the second boundary indication from exceeding the upper boundary of motion or the lower boundary of motion of the detector. As shown in FIG. 2, an upper boundary of motion 261 and a lower boundary of motion 262 of the detector are superimposed and displayed on the captured image, and the upper boundary 261 and the lower boundary 262 are displayed as line segments parallel to the width direction W of the captured image (the width direction of the subject under examination). The display modes of said line segments are different from the line segment display modes of the first boundary indication and the second boundary indication. For example, the line segments are different in color, or the upper and lower boundaries are solid line segments, while the first boundary indication and the second boundary indication are dashed line segments, etc. The embodiments of the present application are not limited thereto. When the position of the first boundary indication is adjusted to be higher than the upper boundary 261, if the move-up marker continues to be clicked or the first boundary indication is dragged upward, then the position of the first boundary indication remains unchanged at the upper boundary 261. When the position of the second boundary indication is adjusted to be lower than the lower boundary 262, if the move-down marker continues to be clicked or the second boundary indication is dragged downward, then the position of the second boundary indication remains unchanged at the lower boundary 262.

In some embodiments, when the exposure region is not completely displayed in the captured image within the current viewable range, or when it is necessary to make a major adjustment to the position of the exposure region, it is possible to adjust the viewable range of the camera first, then re-acquire the captured image, and determine the positions of the first boundary indication and the second boundary indication on the re-acquired image to determine the exposure region. The input device is further used to receive an input operation (a third input operation) for adjusting the viewable range of the camera, and the display updates and displays the captured image according to the input operation for adjusting the viewable range of the camera.

In some embodiments, the third input operation includes triggering an camera field-of-view adjustment marker. The camera field-of-view adjustment marker includes a virtual key or other graphical objects, and may be located on the captured image or the operating region 23. The third input operation for triggering includes clicking a corresponding marker by moving a cursor, or touching or operating (e.g., dragging, etc.) the marker.

For example, as shown in FIG. 2, the operating region 23 of the graphical user interface includes an operating bar 27 and an camera field-of-view adjustment marker 28 superimposed and displayed on the operating bar. The position of the camera field-of-view adjustment marker in the operating bar is adjusted (such as by dragging or sliding), so as to adjust the viewable range of the camera (or to control vertical movement of the suspension apparatus). By dragging the camera field-of-view adjustment marker 28 toward an end A of the operating bar 27, the viewable range of the camera is adjusted upward (to capture a position on the subject under examination closer to the head), and by dragging the camera field-of-view adjustment marker 28 toward an end B of the operating bar 27, the viewable range of the camera is adjusted downward (to capture a position on the subject under examination closer to the foot).

For example, for the implementation of the camera field-of-view adjustment marker, reference may be made to the virtual key of the first marker. By clicking the move-up (or replaced with left/right) marker, the viewable range of the camera is adjusted upward (to capture a position on the subject under examination closer to the head), and by clicking the move-down (or replaced with right/left) marker, the viewable range of the camera is adjusted downward (to capture a position on the subject under examination closer to the foot).

In some embodiments, when the input device receives the input operation for adjusting the viewable range of the camera, the position of the first boundary indication and the position of the second boundary indication change along with the position of the anatomical site, and the position of the first boundary indication and the position of the second boundary indication are fixed relative to the position of the anatomical site in the captured image. The specific implementations thereof are as described previously, and will not be repeated here.

In some embodiments, the adjustment of the viewable range of the camera may also restrict the positions of the boundary indications, that is to say, in some cases, when the adjustment of the viewable range of the camera causes the positions of the boundary indications to exceed the boundaries of motion of the detector or the edges of the viewable range, the positions of the boundary indications will be restricted by the positions of the boundaries of motion of the detector or the edges of the viewable range, and will thus change relative to the anatomical position in the captured image. When the viewable range of the camera is adjusted such that the position of the first boundary indication exceeds an upper boundary of motion of the detector, the controller restricts the position of the first boundary indication to remain at the upper boundary of motion of the detector. Alternatively, when the viewable range of the camera is adjusted such that the position of the first boundary indication exceeds an upper edge of the viewable range, the controller restricts the position of the first boundary indication to remain at the upper edge of the viewable range. When the viewable range of the camera is adjusted such that the position of the second boundary indication exceeds a lower boundary of motion of the detector, the controller restricts the position of the position of the second boundary indication to remain at the lower boundary of motion of the detector, or, when the viewable range of the camera is adjusted such that the position of the second boundary indication exceeds a lower edge of the viewable range, the controller restricts the position of the second boundary indication to remain at the lower edge of the viewable range.

For example, before the viewable range of the camera is adjusted, the first boundary indication is located at the position of the car bone of the subject under examination in the captured image, and after the viewable range of the camera is adjusted, the position of the car bone of the subject under examination in the captured image moves upward. If the first boundary indication moves upward along with the position of the car bone, the first boundary indication will exceed the foregoing upper boundary of motion of the detector. Thus, the position of the first boundary indication remains at the upper boundary of motion of the detector, and will no longer move upward along with the car bone. Alternatively, if the first boundary indication moves upward along with the position of the car bone, the first boundary indication will exceed the upper edge of the viewable range (that is, the car bone is no longer included in the viewable range or in the captured image). Thus, the position of the first boundary indication remains at the upper edge of the viewable range.

For example, before the viewable range of the camera is adjusted, the second boundary indication is located at the position of the ankle bone of the subject under examination in the captured image, and after the viewable range of the camera is adjusted, the position of the ankle bone of the subject under examination in the captured image moves downward. If the second boundary indication moves downward along with the position of the ankle bone, the second boundary indication will exceed the foregoing lower boundary of motion of the detector. Thus, the position of the second boundary indication remains at the lower boundary of motion of the detector, and will no longer move downward along with the ankle bone. Alternatively, if the second boundary indication moves downward along with the position of the ankle bone, the second boundary indication will exceed the lower edge of the viewable range (that is, the ankle bone is no longer included in the viewable range or in the captured image). Thus, the position of the second boundary indication remains at the lower edge of the viewable range.

In some embodiments, as shown in FIG. 2, the graphical user interface may further include an indication position reset marker 29, and when the input device receives an input operation (a fourth input operation) for triggering the indication position reset marker, the controller resets the positions of the first boundary indication and the second boundary indication back to initial positions. For example, the indication position reset marker 29 includes a virtual key or other graphical objects, and the indication position reset marker 29 may be located on the captured image or the operating region 23. The input operation for triggering (the fourth input operation) includes clicking a corresponding marker by moving a cursor, or touching or operating the marker. When the indication position reset marker 29 is triggered, the positions of the first boundary indication and the second boundary indication return to the foregoing initialized positions, thereby making the adjustment of the positions of the boundary indications more flexible.

In some embodiments, as shown in FIG. 2, the graphical user interface further includes an indication position confirmation marker 30. When the input device receives an input operation (a fifth input operation) for triggering the indication position confirmation marker, the controller locks the positions of the first boundary indication and the second boundary indication, and after the controller locks the position of the first boundary indication and the position of the second boundary indication, the controller determines the position of the anatomical site corresponding to the position of the first boundary indication and the position of the second boundary indication in the captured image. When the position of the anatomical site changes in the captured image, the position of the first boundary indication and the position of the second boundary indication change along with the position of the anatomical site. The specific implementations thereof are as described previously, and will not be repeated here. For example, the indication position confirmation marker 30 includes a virtual key or other graphical objects, and the indication position confirmation marker 30 may be located on the captured image or the operating region 23. The input operation for triggering (the fifth input operation) includes clicking a corresponding marker by moving a cursor, or touching or operating the marker. When the indication position confirmation marker 30 is triggered, the positions of the first boundary indication and the second boundary indication will be locked, and cannot be adjusted again. At this time, the controller may determine the size of the exposure region according to the locked positions of the first boundary indication and the second boundary indication. For example, the distance between the first boundary indication and the second boundary indication is the length of the exposure region. The length of the exposure region may be used to determine the quantity of sub-medical images, which will be specifically described later.

In the above example, the first boundary indication 21 and the second boundary indication 22 are displayed as line segments, but the embodiments of the present application are not limited thereto. For example, positions overlapping with the corresponding anatomical site on the first boundary indication and the second boundary indication are displayed as the contour of the anatomical site, and the position of the contour is related to thickness information of the subject under examination, which will be described below by way of example.

In some embodiments, a 3D point cloud image or a depth image of the subject under examination may be obtained according to the camera, and the thickness information of the subject under examination may be acquired according to the 3D point cloud image or the depth image. The thickness information represents the distance from the front (a first surface) to the back (a detector surface, also called a second surface) of the subject under examination. The thickness information corresponding to different anatomical sites on the subject under examination may be different. Since the distance between the ray source and the first surface, the distance between the ray source and the second surface, and the distance between the first surface and the second surface are all known quantities, it is possible to calculate, according to the principle of mathematical similar triangles in combination with the thickness information, a plurality of second positions obtained after a first position (a certain anatomical site) on the first surface has been mapped to the second surface. According to the plurality of second positions in combination with the corresponding thickness information, a plurality of third positions are calculated after the plurality of second positions have been mapped back to the first surface. The plurality of third positions can reflect information about the contour (or real-time boundary) of the anatomical site.

Figure 10:
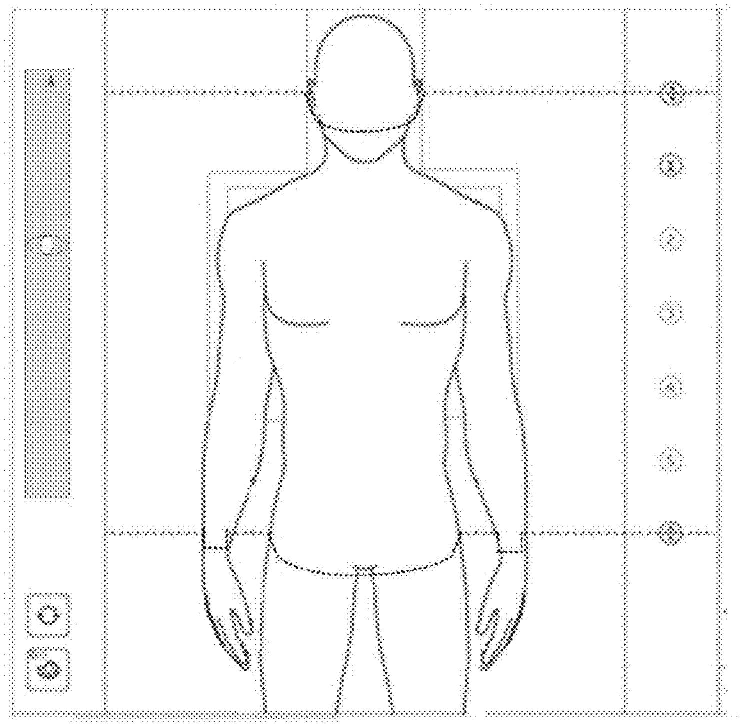
FIG. 10 is a schematic diagram of a graphical user interface of an embodiment of the present application.

FIG. 10 is a schematic diagram of a graphical user interface according to an embodiment of the present application. As shown in FIG. 2, when the first boundary indication and the second boundary indication are line segments, the first boundary indication passes through the middle position between the eyebrows (a first position), and the second boundary indication passes through the position of the coccyx (a first position). According to the foregoing method, a plurality of second positions obtained after the middle position between the eyebrows has been mapped to the second surface are calculated, and a plurality of third positions obtained after the plurality of second positions have been mapped back to the first surface are calculated. A curve is obtained by connecting the plurality of third positions, and replaces part of a line segment that overlaps with the corresponding anatomical site on the first boundary indication in FIG. 2, so as to obtain the first boundary indication in FIG. 10. As shown in FIG. 10, the position overlapping with the head on the first boundary indication is displayed as the contour of the head, thereby reflecting the thickness information of the head. According to the foregoing method, a plurality of second positions obtained by mapping the positions of the coccyx and carpus to the second surface are calculated, and a plurality of third positions obtained by mapping the plurality of second positions back to the first surface are calculated. Curves are obtained by connecting the plurality of third positions, and replace parts of a line segment that overlap with the buttocks and arms on the second boundary indication in FIG. 2, so as to obtain the second boundary indication in FIG. 10. As shown in FIG. 10, the positions overlapping with the buttocks and arms on the second boundary indication are displayed as the contours of the buttocks and arms, reflecting the thickness information of the buttocks and arms, respectively. The above first position may be determined as required. For example, the first position may be a center position among positions overlapping with corresponding anatomical sites on the first boundary indication and the second boundary indication in FIG. 2.

Given that the captured image is a 2D planar image, the positions overlapping with the corresponding anatomical sites on the first boundary indication and the second boundary indication are displayed as the contours of the anatomical sites, such that the exposure region is displayed in a more stereoscopic manner, and the operator may more intuitively view the thickness information of the anatomical sites on the boundary positions of the exposure region.

In some embodiments, positions overlapping with the corresponding anatomical sites on the foregoing upper edge, lower edge, upper boundary and lower boundary may also be displayed as the contours of the anatomical sites, implementations of which are similar to those of the first boundary indication and the second boundary indication, and will not repeated here.

It should be noted that the graphical user interface in the embodiment of the present application may include one or more of the indication position reset marker 29, the indication position confirmation marker 30, the camera field-of-view adjustment marker 28, the upper boundary of motion 261 and the lower boundary of motion 262 of the detector, the first marker 24, the second marker 25, and the operating region 23 described above, or may not include the above markers and boundaries. The embodiments of the present application are not limited thereto. Further, the above markers may also be located in a second region 202 of the graphical user interface to be described later, which will be specifically described later.

In some embodiments, the controller may determine the size of the exposure region according to the finally determined position of the first boundary indication and the finally determined position of the second boundary indication, and determine a first quantity of sub-medical images according to the size of the exposure region and the size of the detector. The medical image is formed by stitching the first quantity of sub-medical images together. For example, the height direction of the detector is H, the length of the exposure region is LD, and the first quantity N is an integer greater than or equal to LD/H. Alternatively, when the first quantity is determined, it is also necessary to consider the distance from the detector to the region of interest, the distance from the focal point to the detector, and the size of the overlapping portion of two adjacent sub-medical images when the sub-medical images are stitched. Reference may be made to the related art for details, and the embodiments of the present application are not limited thereto. As shown in FIG. 2, after the first quantity of sub-medical images is determined, image numbers of the respective sub-medical images may be further displayed on the operating region 23 of the first region 201. For example, when the first quantity is five, five sub-medical images need to be exposed, and the final medical image is obtained by stitching the five sub-medical images together. Image numbers ①, ②, ③, ④ and ⑤ of the five sub-medical images can be respectively displayed on the operating region 23. In this way, the operator can intuitively and conveniently determine the approximate position of each sub-medical image corresponding to the captured image.

Figure 4:
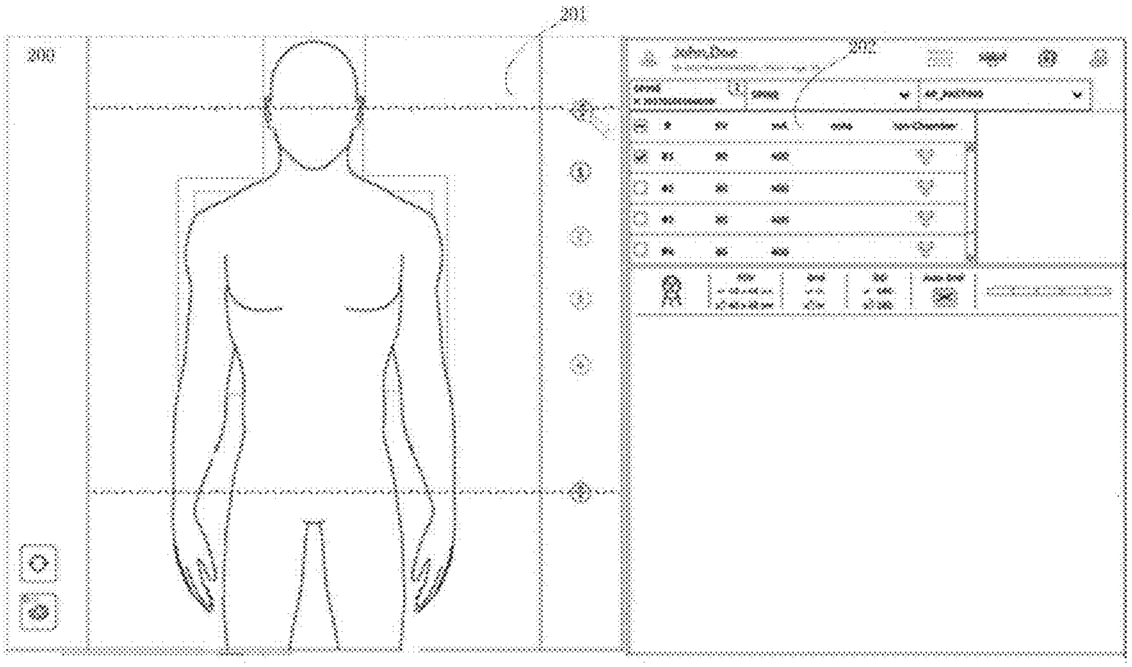
FIG. 4 is a schematic diagram of a graphical user interface of an embodiment of the present application.

In some embodiments, FIG. 4 is a schematic diagram of a graphical user interface according to an embodiment of the present application. As shown in FIG. 4, in order to adjust imaging parameters of the first quantity of sub-medical images conveniently, after the first quantity of sub-medical images are determined, the graphical user interface may further include a second region 202, and exposure parameters of respective sub-medical images (#1, #2, #3 and #4) among the first quantity (4) of sub-medical images may be simultaneously displayed on the second region 202, the exposure parameters including at least one of a tube voltage (KV), a tube current (mA), exposure time (mAs), and an automatic exposure control ionization chamber (AEC ion-chamber). The operator can adjust the respective exposure parameters in the second region 202. Reference may be made to the related art for details, and the embodiments of the present application are not limited thereto.

In some embodiments, for the automatic exposure control ionization chamber among the exposure parameters, a switch state thereof may be further configured in the first region 201, which will be described in detail below.

In some embodiments, the medical imaging system may include a plurality of (Z) automatic exposure control ionization chambers (e.g., arranged in the detector). The plurality of automatic exposure control ionization chambers may be distributed across different positions on the detector. The X-ray tube can produce X rays, and the automatic exposure control ionization chambers can detect the amount of received X-rays after passing through the subject under examination. If the amount of X-rays exceeds a predetermined amount, then the automatic exposure control ionization chambers can send a notification signal to the controller, and the controller can stop the irradiation of X-rays. In this way, the amount of emitted X-rays is adjusted by means of the automatic exposure control ionization chambers. Before exposure, the operator may select an automatic exposure control ionization chamber at a position corresponding to the position of the region of interest to perform automatic exposure control.

Figure 5:
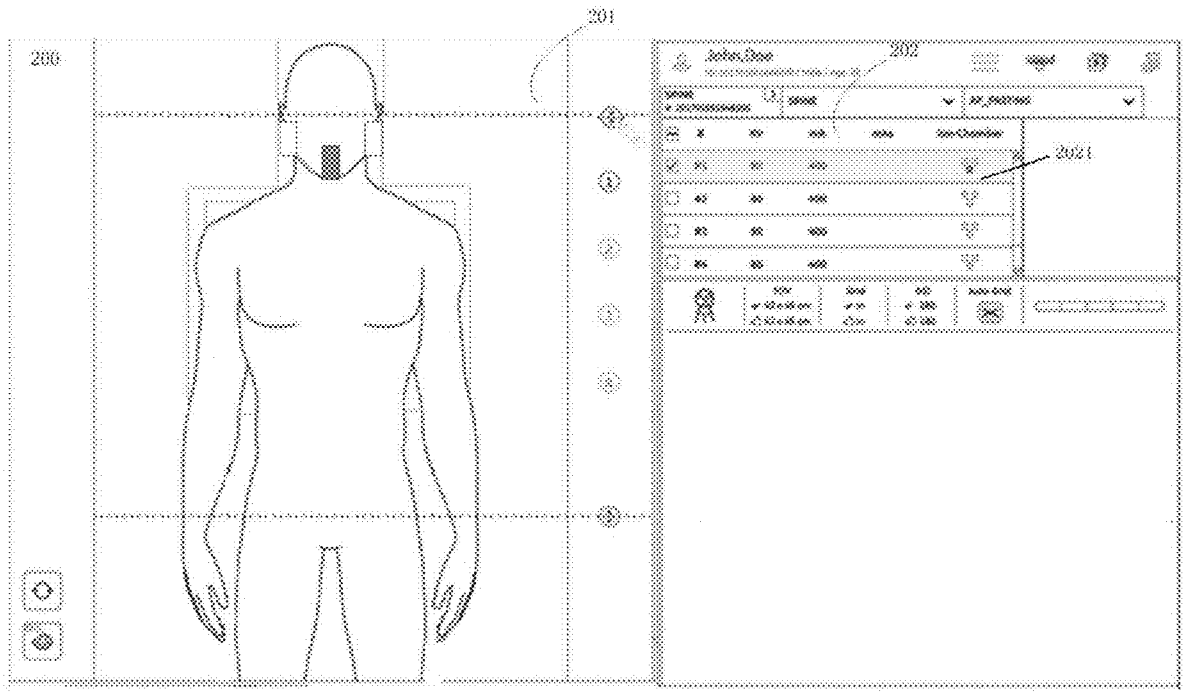
FIG. 5 is a schematic diagram of a graphical user interface of an embodiment of the present application.
Figure 6:
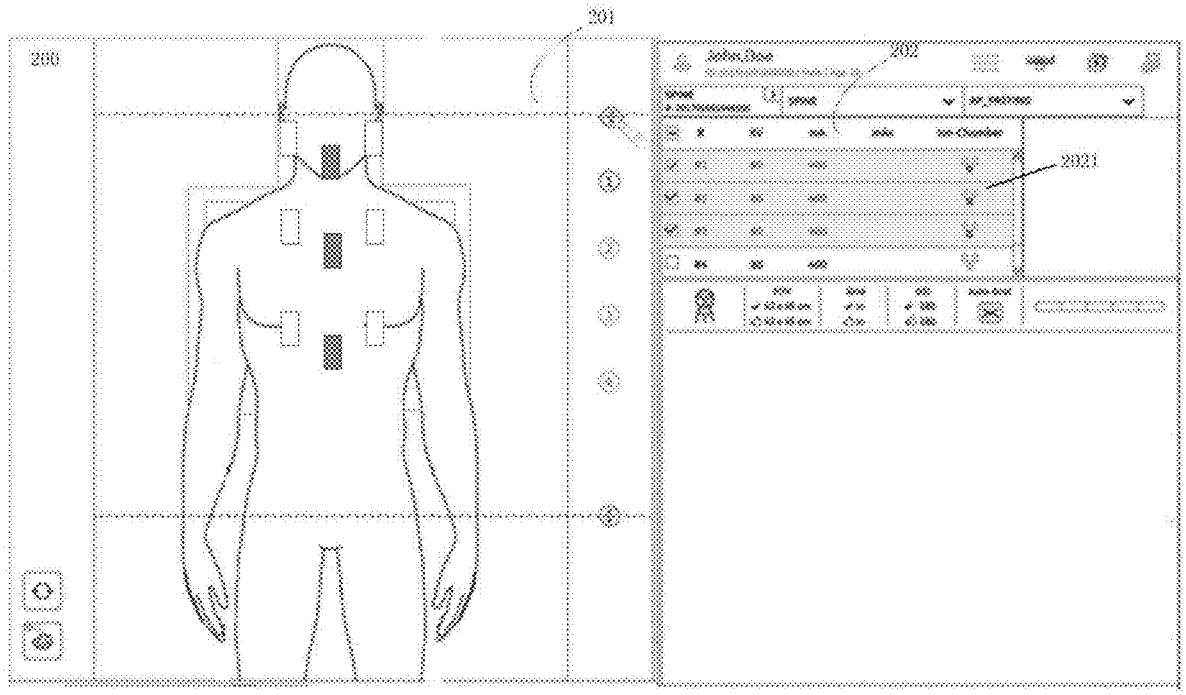
FIG. 6 is a schematic diagram of a graphical user interface of an embodiment of the present application.
Figure 7:
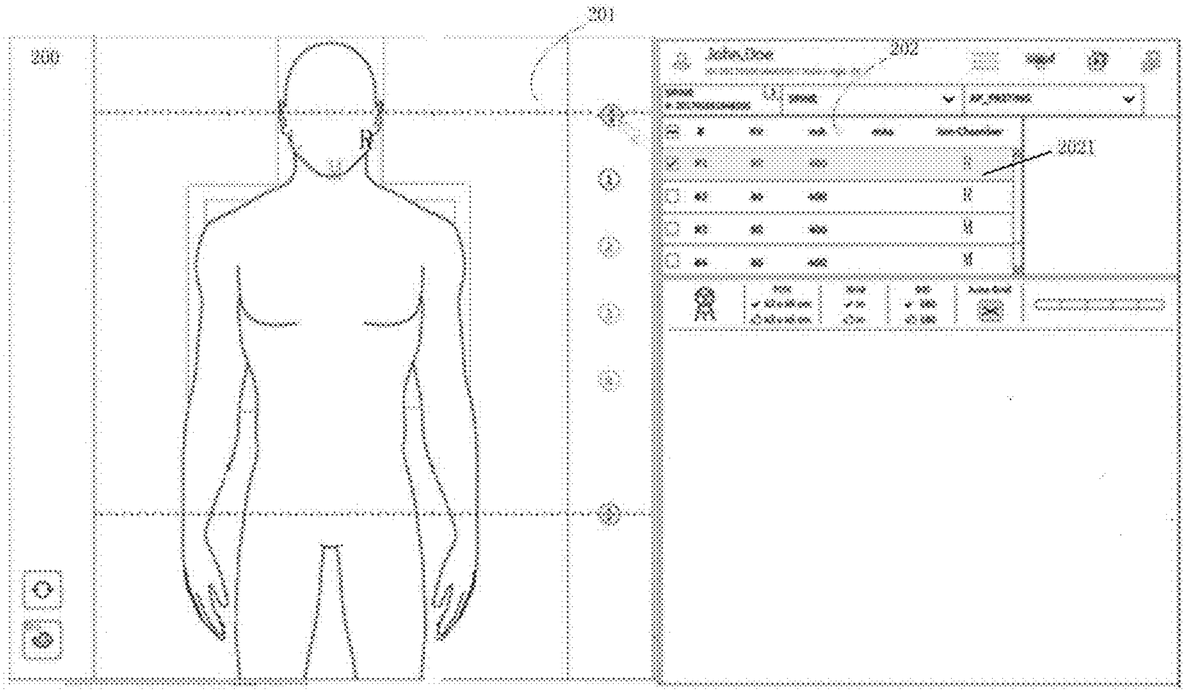
FIG. 7 is a schematic diagram of a graphical user interface of an embodiment of the present application.
Figure 8:
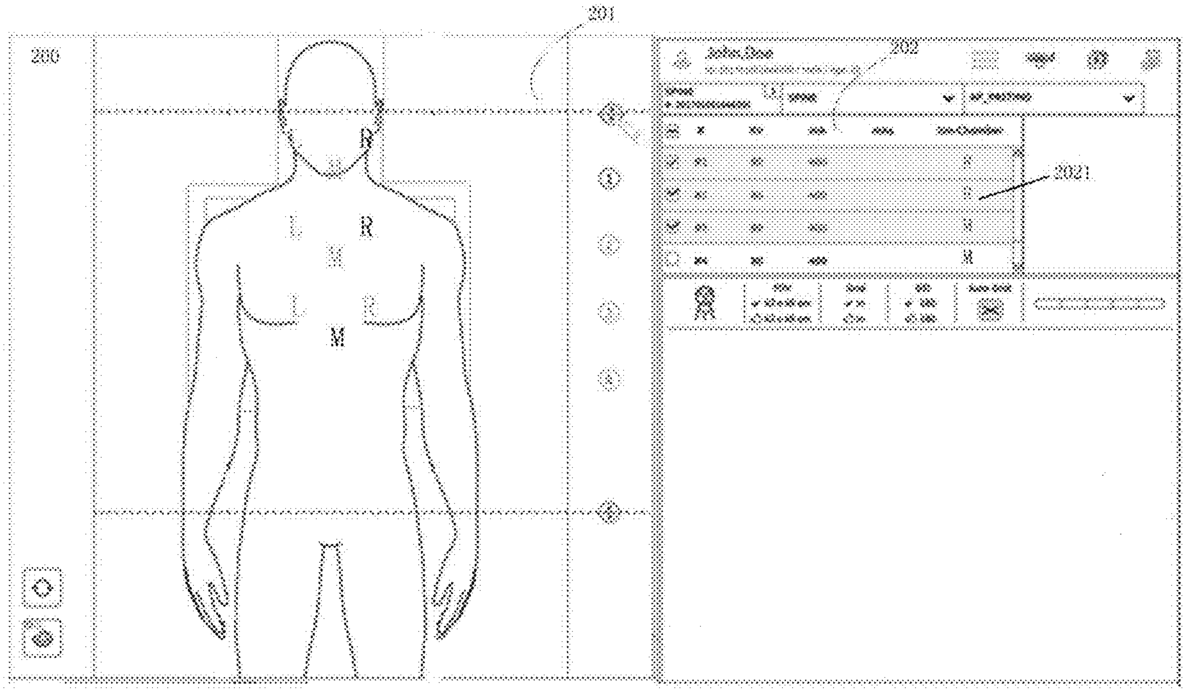
FIG. 8 is a schematic diagram of a graphical user interface of an embodiment of the present application.

In some embodiments, the input device may receive an input operation for selecting a sub-medical image. For example, by clicking a column where a sub-medical image is located on the above second region 202, or by clicking the image number of a sub-medical image on the operating region 23, one or more sub-medical images are selected. After the selection, the column where the sub-medical images are located on the second region 202 may be highlighted. After the sub-medical images are selected, markers for the Z automatic exposure control ionization chambers are superimposed and displayed at the positions corresponding to the sub-medical images in the captured image, respectively. The positions for superimposition and display do not represent the actual positions thereof, but only represent the relative positions of the Z automatic exposure control ionization chambers. One rectangular box may be used as a marker for one automatic exposure control ionization chamber, or different graphical objects may also be used as markers for different automatic exposure control ionization chambers, and the embodiments of the present application are not limited thereto. FIGS. 5 and 6 are schematic diagrams of a graphical user interface according to an embodiment of the present application. Taking Z=3 as an example, three automatic exposure control ionization chambers are represented by using three rectangular boxes, and are respectively superimposed and displayed on the captured image in a schematic manner. As shown in FIG. 5, only the first sub-medical image is selected (the column corresponding to the sub-medical image on the second region 202 may be highlighted). Therefore, three markers (three rectangular boxes) for automatic exposure control ionization chambers are superimposed and displayed at positions corresponding to the first sub-medical image in the captured image. As shown in FIG. 6, three sub-medical images are selected (the columns corresponding to the three sub-medical images on the second region 202 may be highlighted). Therefore, three markers (three rectangular boxes) for automatic exposure control ionization chambers are respectively superimposed and displayed at positions corresponding to each sub-medical image in the captured image. FIGS. 7 and 8 are schematic diagrams of a graphical user interface according to an embodiment of the present application, and are different from FIGS. 5 and 6 in that the markers for automatic exposure control ionization chambers are represented by using different letters. Taking Z=3 as an example, the markers for three automatic exposure control ionization chambers are represented by using R, M and L, respectively.

In some embodiments, the display also needs to superimpose and display the switch states of Z automatic exposure control ionization chambers corresponding to the one or more selected sub-medical images on a captured image, wherein an ON state or an OFF state may be distinguished by the style change of the foregoing markers for the automatic exposure control ionization chambers. The switch state does not represent the current switch state of the automatic exposure control ionization chamber, but the switch state of the automatic exposure control ionization chamber after the exposure operation starts. The ON state represents that the corresponding automatic exposure control ionization chamber is selected and used for automatic exposure control after the exposure operation starts, and the OFF state represents that the corresponding automatic exposure control ionization chamber is not selected and is not used for automatic exposure control after the exposure operation starts. As shown in FIGS. 5 and 6, the ON state or OFF state may be distinguished by using rectangles of different fill colors. For example, a white rectangle is used to represent the OFF state (not selected), a dark rectangle is used to represent the ON state (selected), and vice versa. The embodiments of the present application are not limited thereto, and the ON state or OFF state may also be distinguished by using rectangles of different sizes. For example, a small rectangle can be used to represent the OFF state (not selected), and a large rectangle can be used to represent the ON state (selected). As shown in FIGS. 7 and 8, the ON state or OFF state may be distinguished by using letters of different colors. For example, gray letters can be used to represent the OFF state (not selected) and black letters can be used to represent the ON state (selected), and the like, and examples are no longer provided for each case here.

In some embodiments, when the markers for the plurality of automatic exposure control ionization chambers are initially superimposed and displayed, the same may all be in the OFF state by default, or one thereamong may be in the ON state by default and others in the OFF state by default, and the embodiments of the present application are not limited thereto.

In some embodiments, the input device may receive an input operation (a sixth input operation) for setting the switch states of the plurality of automatic exposure control ionization chambers. The sixth input operation includes triggering (by moving a cursor to perform clicking or touching) one of the superimposed and displayed markers for the Z automatic exposure control ionization chambers. After the input operation is received, the controller selects, according to the received input operation for setting the switch states of the plurality of automatic exposure control ionization chambers, an automatic exposure control ionization chamber in an ON state to perform exposure time control. For example, after the input operation is received, the mode of the triggered marker for the automatic exposure control ionization chamber changes, which represents that the switch state is switched. For example, when the marker for the automatic exposure control ionization chamber is a white rectangle, after the marker is triggered, the marker is changed to a dark rectangle, which represents that the automatic exposure control ionization chamber at the position corresponding to the marker is selected. The automatic exposure control ionization chamber is in the ON state for automatic exposure control after the exposure operation starts.

In some embodiments, when only one automatic exposure control ionization chamber can be selected to be in the ON state for one sub-medical image, the automatic exposure control ionization chamber corresponding to the triggered marker for the automatic exposure control ionization chamber is changed to the ON state (e.g., changing from a white rectangle to a dark rectangle) upon receiving the sixth input operation, and when an automatic exposure control ionization chamber corresponding to a non-triggered marker for the automatic exposure control ionization chamber is in the ON state (i.e., a non-triggered dark rectangle is still present), synchronously with the sixth input operation, the controller changes the automatic exposure control ionization chamber corresponding to the non-triggered marker for the automatic exposure control ionization chamber to the OFF state, that is, the display synchronously updates and displays the mode of the non-triggered marker for the automatic exposure control ionization chamber (e.g. changing from a dark rectangle to a white rectangle).

In some embodiments, as shown in FIGS. 5 to 8, the exposure parameter display region in the second region 202 of the graphical user interface may also synchronously display the switch states 2021 of a plurality of automatic exposure control ionization chambers corresponding to respective sub-medical images. The switch states of the plurality of automatic exposure control ionization chambers displayed in the second region 202 and corresponding to the respective sub-medical images are the same as the switch states of the plurality of automatic exposure control ionization chambers superimposed and displayed at the positions of the corresponding sub-medical images of the captured image.

The above input operations may also be inputted by means of voice, and the embodiments of the present application are not limited thereto.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

Figure 9:
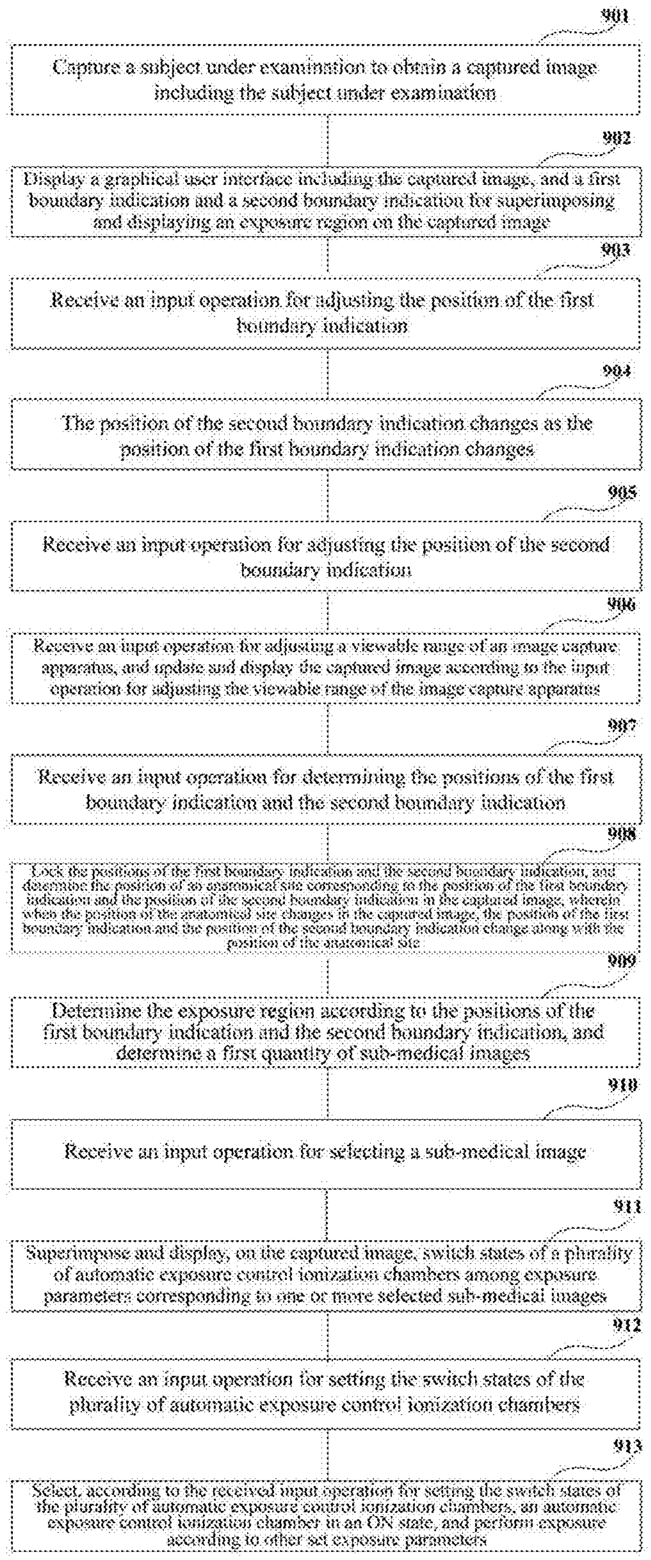
FIG. 9 is a schematic diagram of an operating method for a medical imaging system according to an embodiment of the present application.

An embodiment of the present application further provides an operating method for a medical imaging system. The same content as that of the embodiments of the foregoing aspects is not repeated herein. FIG. 9 is a schematic diagram of an operating method for a medical imaging system according to an embodiment of the present application. As shown in FIG. 9, the method includes:

- 901, capturing a subject under examination to obtain a captured image including the subject under examination;
- 902, displaying a graphical user interface including the captured image, and a first boundary indication and a second boundary indication for superimposing and displaying an exposure region on the captured image (displaying initial positions);
- 903, receiving an input operation for adjusting the position of the first boundary indication;
- 904, controlling the position of the second boundary indication to change along with the change of the position of the first boundary indication so that the distance between the first boundary indication and the second boundary indication remains unchanged;
- 905, receiving an input operation for adjusting the position of the second boundary indication;
- 906, receiving an input operation for adjusting a viewable range of an camera, and updating and displaying the captured image according to the input operation for adjusting the viewable range of the camera, wherein the position of the first boundary indication and the position of the second boundary indication are fixed relative to an anatomical position in the captured image, and if there is a need to re-adjust the position of the first boundary indication or the position of the second boundary indication, the process may return to 903-905;
- 907, receiving an input operation for determining the positions of the first boundary indication and the second boundary indication, e.g., an input operation for triggering the indication position confirmation marker;
- 908, the controller locking the positions of the first boundary indication and the second boundary indication, and determining the position of an anatomical site corresponding to the position of the first boundary indication and the position of the second boundary indication in the captured image, wherein when the position of the anatomical site changes in the captured image, the position of the first boundary indication and the position of the second boundary indication change along with the position of the anatomical site;
- 909, determining the exposure region according to the positions of the first boundary indication and the second boundary indication, and determining a first quantity of sub-medical images;
- 910, receiving an input operation for selecting a sub-medical image;
- 911, superimposing and displaying, on the captured image, switch states of a plurality of automatic exposure control ionization chambers among exposure parameters corresponding to one or more selected sub-medical images;
- 912, receiving an input operation for setting the switch states of the plurality of automatic exposure control ionization chambers; and
- 913, selecting, according to the received input operation for setting the switch states of the plurality of automatic exposure control ionization chambers, an automatic exposure control ionization chamber in an ON state, and performing exposure according to other set exposure parameters.

It should be noted that FIG. 9 above merely schematically illustrates an embodiment of the present application, but the present application is not limited thereto. For example, the order of execution between the respective operations may be appropriately adjusted. For example, 905 may be executed before 903. In addition, it is also possible to further increase some other operations or skip some of the existing operations, for example, skipping at least one step of 903 to 907 or 909 to 913, etc. Those skilled in the art could make appropriate variations according to the above content, rather than being limited by the disclosure of FIG. 9 described above.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

An embodiment of the present application further provides a graphical user interface. The graphical user interface includes a first region displaying a captured image, and a first boundary indication and a second boundary indication for superimposing and displaying an exposure region on the captured image, wherein when the position of an anatomical site corresponding to the position of the first boundary indication and the position of the second boundary indication changes in the captured image, the position of the first boundary indication and the position of the second boundary indication change along with the position of the anatomical site.

In some embodiments, the graphical user interface further includes at least one of an upper boundary of motion and a lower boundary of motion of a detector, the boundaries being superimposed and displayed on the captured image.

In some embodiments, the graphical user interface further includes an indication position confirmation marker, and the positions of the first boundary indication and the second boundary indication are locked by means of triggering the indication position confirmation marker.

In some embodiments, the graphical user interface further includes an camera field-of-view adjustment marker, and a viewable range of an camera is adjusted by means of triggering the camera field-of-view adjustment marker.

In some embodiments, the graphical user interface further includes an indication position reset marker, and the positions of the first boundary indication and the second boundary indication are reset back to initial positions by means of triggering the indication position reset marker.

In some embodiments, the graphical user interface further includes markers for switch states of a plurality of automatic exposure control ionization chambers corresponding to one or more selected sub-medical images, the markers being superimposed and displayed on the captured image, and the states of the respective automatic exposure control ionization chambers corresponding to the one or more selected sub-medical images are set to ON or OFF by means of triggering the markers for the switch states.

In some embodiments, the graphical user interface further includes a second region, an operating region, a first marker, and a second marker, etc., and for implementations of each of the above regions or markers or boundaries or boundary indications, reference may be made to the foregoing embodiments (as shown in any one of FIGS. 2 to 8), and details thereof will not be repeated here.

According to the medical imaging system, the operating method therefor, and the graphical user interface provided in the present application, when the position of the anatomical site changes in the captured image, the position of the first boundary indication and the position of the second boundary indication for the exposure region change along with the position of the anatomical site, thereby avoiding exposure region errors caused by the movement of the subject under examination or the adjustment of the viewable range of the camera.

In addition, when the position of the first boundary indication is adjusted, the position of the second boundary indication is controlled to change along with the change of the position of the first boundary indication so that the distance between the first boundary indication and the second boundary indication remains unchanged, thereby simplifying adjustment steps, and quickly and conveniently adjusting the position of the exposure region.

In addition, when the position of the second boundary indication is adjusted, the position of the first boundary indication remains unchanged, thereby making the adjustment of the position of the boundary indication more flexible and reducing the time for repeated adjustments.

In addition, when the position of the second boundary indication is adjusted to exceed a lower boundary of motion of the detector, the controller restricts downward adjustment of the position of the second boundary indication, and when the position of the first boundary indication is adjusted to exceed an upper boundary of motion of the detector, the controller restricts upward adjustment of the position of the first boundary indication, thereby preventing the exposure region from being located outside the boundary range within which the detector can move.

In addition, at least one of the upper boundary of motion and the lower boundary of motion of the detector is superimposed and displayed on the captured image, thereby reducing the time of unnecessary repeated adjustments.

In addition, the input device is further used to receive an input operation for adjusting the viewable range of the camera, and the display updates and displays the captured image according to the input operation for adjusting the viewable range of the camera. In this way, the problem in which the exposure region is not completely displayed in a captured image within the current viewable range is avoided, and a large adjustment of the position of the exposure region is supported.

In addition, by designing an indication position reset marker, when the indication position reset marker is triggered, the positions of the first boundary indication and the second boundary indication will return to the initialized positions, thereby making the adjustment of the positions of the boundary indications more flexible.

In addition, by designing an indication position confirmation marker, when the indication position confirmation marker is triggered, the positions of the first boundary indication and the second boundary indication are locked, thereby avoiding a change in the positions of the first boundary indication and the second boundary indication caused by unnecessary misoperation.

In addition, the positions overlapping with the corresponding anatomical sites on the first boundary indication and the second boundary indication are displayed as the contours of the anatomical sites, such that the exposure region is displayed in a more stereoscopic manner, and the operator may more intuitively view the thickness information of the anatomical sites on the boundary positions of the exposure region.

In addition, the markers for switch states of the plurality of automatic exposure control ionization chambers are superimposed and displayed on the captured image, and the states of the automatic exposure control ionization chambers corresponding to the second quantity of sub-medical images are set as ON or OFF by triggering the markers for the switch states, thereby allowing the selection of automatic exposure control ionization chambers to be more visual and convenient.

The above apparatus and method of the present application can be implemented by hardware, or can be implemented by hardware in combination with software. The present application relates to the foregoing type of computer-readable program. When executed by a logic component, the program causes the logic component to implement the foregoing apparatus or a constituent component, or causes the logic component to implement various methods or steps as described above. The present application further relates to a storage medium for storing the above program, such as a hard disk, a magnetic disk, an optical disk, a DVD, a flash memory, etc.

The method/apparatus described with reference to the examples of the present application may be directly embodied as hardware, a software module executed by a processor, or a combination of the two. For example, one or more of the functional block diagrams and/or one or more combinations of the functional block diagrams as shown in the drawings may correspond to either software modules or hardware modules of a computer program flow. The foregoing software modules may respectively correspond to the steps shown in the figures. The foregoing hardware modules may be implemented, for example, by firming the foregoing software modules by using a field-programmable gate array (FPGA).

The software modules may be located in a RAM memory, a flash memory, a ROM memory, an EPROM memory, an EEPROM memory, a register, a hard disk, a removable disk, a CD-ROM, or any storage medium in other forms known in the art. The storage medium may be coupled to a processor, so that the processor can read information from the storage medium and can write information into the storage medium. Alternatively, the storage medium may be a constituent component of the processor. The processor and the storage medium may be located in an ASIC. The software module may be stored in a memory of a mobile terminal, and may also be stored in a memory card that can be inserted into a mobile terminal. For example, if a device (such as a mobile terminal) uses a large-capacity MEGA-SIM card or a large-capacity flash memory apparatus, then the software modules may be stored in the MEGA-SIM card or the large-capacity flash memory apparatus.

One or more of the functional blocks and/or one or more combinations of the functional blocks shown in the drawings may be implemented as a general-purpose processor, a digital signal processor (DSP), an application-specific integrated circuit (ASIC), a field-programmable gate array (FPGA) or other programmable logic devices, a discrete gate or transistor logic device, a discrete hardware assembly, or any appropriate combination thereof, which is used for implementing the functions described in the present application. The one or more functional blocks and/or the one or more combinations of the functional blocks shown in the drawings may also be implemented as a combination of computing equipment, such as a combination of a DSP and a microprocessor, a plurality of microprocessors, one or more microprocessors in communication combination with a DSP, or any other such configuration.

The present application is described above with reference to specific embodiments. However, it should be clear to those skilled in the art that the foregoing description is merely illustrative and is not intended to limit the scope of protection of the present application. Various variations and modifications may be made by those skilled in the art according to the principle of the present application, and said variations and modifications also fall within the scope of the present application.

What is claimed is:

1. A medical imaging system, comprising:

an imaging device including an X-ray source and a detector, wherein the X-ray source and the detector are capable of cooperating to acquire a medical image of a subject under examination;

a camera operably connected to the imaging device for capturing the subject under examination to obtain a captured image including the subject under examination;

a display operably connected to the camera for displaying a graphical user interface including the captured image, and a first boundary indication and a second boundary indication for superimposing and displaying an exposure region on the captured image;

an input device operably connected to the display for receiving an input operation for adjusting a position of the first boundary indication and an input operation for adjusting a position of the second boundary indication; and a controller for determining the position of the first boundary indication and the position of the second boundary indication according to the input operations received by the input device, and determining a position of an anatomical site corresponding to the position of the first boundary indication and the position of the second boundary indication in the captured image, wherein when the position of the anatomical site changes in the captured image, the position of the first boundary indication and the position of the second boundary indication change, and wherein when the input device receives the input operation for adjusting the position of the first boundary indication, the controller changes the position of the second boundary indication and the position of the first boundary indication so that a distance between the first boundary indication and the second boundary indication remains unchanged.

2. The medical imaging system of claim 1, wherein when the position of the first boundary indication and the position of the second boundary indication change with the position of the anatomical site, the position of the first boundary indication and the position of the second boundary indication are fixed relative to the position of the anatomical site.

3. The medical imaging system of claim 1, wherein when the position of the second boundary indication and the position of the first boundary indication change to exceed a lower edge of the captured image, the controller controls the position of the second boundary indication to remain unchanged at the lower edge.

4. The medical imaging system of claim 1, wherein when the input device receives the input operation for adjusting the position of the second boundary indication, the position of the first boundary indication remains unchanged.

5. The medical imaging system of claim 1, wherein when the position of the second boundary indication is adjusted to exceed a lower boundary of motion of the detector, the controller restricts downward adjustment of the position of the second boundary indication, and wherein when the position of the first boundary indication is adjusted to exceed an upper boundary of motion of the detector, the controller restricts upward adjustment of the position of the first boundary indication.

6. The medical imaging system of claim 5, wherein the display superimposes and displays on the captured image at least one of the upper boundary of motion and the lower boundary of motion of the detector.

7. The medical imaging system of claim 1, wherein the controller initializes initial positions of the first boundary indication and the second boundary indication according to a center position of the captured image or a site to be imaged.

8. The medical imaging system of claim 1, wherein the graphical user interface includes an indication position reset marker, and when the input device receives an input operation for triggering the indication position reset marker, the controller resets the positions of the first boundary indication and the second boundary indication back to initial positions.

9. The medical imaging system of claim 1, wherein the graphical user interface includes an indication position confirmation marker, and when the input device receives an input operation for triggering the indication position confirmation marker, the controller locks the positions of the first boundary indication and the second boundary indication.

10. The medical imaging system of claim 9, wherein after the controller locks the positions of the first boundary indication and the second boundary indication, the controller determines the position of the anatomical site corresponding to the position of the first boundary indication and the position of the second boundary indication in the captured image, and when the position of the anatomical site changes in the captured image, the position of the first boundary indication and the position of the second boundary indication change.

11. The medical imaging system of claim 1, wherein the input device is further used to receive an input operation for adjusting a viewable range of the camera, and the display updates and displays the captured image according to the input operation for adjusting the viewable range of the camera.

12. The medical imaging system of claim 11, wherein the graphical user interface includes an operating bar and a camera field-of-view adjustment marker superimposed and displayed on the operating bar, and wherein the viewable range of the camera is adjusted by means of adjusting the position of the camera field-of-view adjustment marker in the operating bar.

13. A medical imaging system, comprising:

a display unit including a graphical user interface, the graphical user interface includes a region for displaying a captured image, and a first boundary indication and a second boundary indication for superimposing and displaying an exposure region on the captured image, wherein when the position of an anatomical site corresponding to the position of the first boundary indication and the position of the second boundary indication changes in the captured image, the position of the first boundary indication and the position of the second boundary indication change along with the position of the anatomical site, and wherein the graphical user interface includes an indication position confirmation marker, and wherein the positions of the first boundary indication and the second boundary indication are locked by triggering the indication position confirmation marker.

14. The medical imaging system of claim 13, wherein the graphical user interface includes an upper boundary of motion and a lower boundary of motion of a detector, the boundaries being superimposed and displayed on the captured image.

15. The medical imaging system of claim 13, wherein the graphical user interface includes a camera field-of-view adjustment marker, and wherein a viewable range of a camera is adjusted by triggering the camera field-of-view adjustment marker.

16. The medical imaging system of claim 13, wherein the graphical user interface includes an indication position reset marker, and the positions of the first boundary indication and the second boundary indication are reset back to initial positions by triggering the indication position reset marker.

17. The medical imaging system of claim 13, wherein the graphical user interface includes markers for switch states of a plurality of automatic exposure control ionization chambers corresponding to one or more selected sub-medical images, the markers being superimposed and displayed on the captured image, and the states of the respective automatic exposure control ionization chambers corresponding to the one or more selected sub-medical images are set to ON or OFF by means of triggering the markers for the switch states.

18. A method for operating a medical imaging system, the method comprising:

capturing a subject under examination to obtain a captured image comprising the subject under examination;

displaying a graphical user interface including the captured image, and a first boundary indication and a second boundary indication for superimposing and displaying an exposure region on the captured image;

receiving an input operation for adjusting a position of the first boundary indication and an input operation for adjusting a position of the second boundary indication; and determining the position of the first boundary indication and the position of the second boundary indication according to the received input operations, and determining the position of an anatomical site corresponding to the position of the first boundary indication and the position of the second boundary indication in the captured image, wherein when the position of the anatomical site changes in the captured image, the position of the first boundary indication and the position of the second boundary indication change, and wherein initial positions of the first boundary indication and the second boundary indication are initialized according to a center position of the captured image or a site to be imaged.

* * * * *